(12) United States Patent
Puddicombe et al.

(10) Patent No.: US 7,312,047 B2
(45) Date of Patent: Dec. 25, 2007

(54) SCREENING ASSAY FOR IMPROVEMENT OF EPITHELIAL BARRIER FUNCTION

(75) Inventors: Sarah M. Puddicombe, Hampshire (GB); Donna Elizabeth Davies, Wiltshire (GB); Stephen Holgate, Hampshire (GB)

(73) Assignee: University of Southampton, Hampshire (GB)

( * ) Notice: Subject to any disclaimer, the term of this patent is extended or adjusted under 35 U.S.C. 154(b) by 309 days.

(21) Appl. No.: 11/135,339

(22) Filed: May 24, 2005

(65) Prior Publication Data

US 2006/0269909 A1 Nov. 30, 2006

(51) Int. Cl.
*C12Q 1/02* (2006.01)
(52) U.S. Cl. .......................................... 435/29
(58) Field of Classification Search ............... None
See application file for complete search history.

(56) References Cited

OTHER PUBLICATIONS

Holgate, S.T. et al., "Mechanisms of Airway Epithelial Damage: Epithelial-Mesenchymal Interaction in the Pathogenesis of Asthma," (Eur Respir J), 2003, vol. 22 Suppl. 44, pp. 24s-29s.*
H. C. Atherton et al., "IL-13-induced changes in the goblet cell density of human bronchial epithelial cell cultures: MAP kinase and phosphatidylinositol 3-kinase regulation", Am. J. Physiol. Lung Cell Mol. Physiol., vol. 285, pp. L730-739, 2003.
H. Bayram et al., "Effect of ozone and nitrogen dioxide on the permeability of bronchial epithlial cell cultures of non-asthmatic and asthmatic subjects", Clin. Exp. Allergy, vol. 32, pp. 1285-1292, 2002.
P. Demoly et al., "Cell Proliferation in the Bronchial Mucosa of Asthmatics and Chronic Bronchitics", Am. J. Respir. Crit. Care Med., vol. 150, pp. 214-217, 1994.
V. J. Erpenbeck et al., "Local release of eosinophil peroxidase following segmental allergen provocation in asthma", Clin. Exp. Allergy, vol. 33, pp. 331-336, 2003.
A. L. James et al., "The Pathology of Fatal Asthma", Eds: Marcel Dekker, New York, pp. 1-26, 1998.
M. Kondo et al., "Interleukin-13 Induces Goblet Cell Differentiation in Primary Cell Culture from Guinea Pig Tracheal Epithelium", Am. J. Respir. Cell Mol. Biol., vol. 27, pp. 536-541, 2002.
L. A. Laitinen et al., "Damage of the Airway Eptihelium and Bronchial Reactivity in Patients with Asthma[1-3]", Am. Rev. Respir. Dis., vol. 131, pp. 599-606, 1985.
J. Leoukili et al., "IL-13 Alters Mucociliary Differentiation and Ciliary Beating of Human Respiratory Epithelial Cells", The Journal of Clinical Investigation, vol. 108, No. 12, pp. 1817-1824, Dec. 2001.

(Continued)

*Primary Examiner*—Ralph Gitomer
*Assistant Examiner*—Amanda P. Wood
(74) *Attorney, Agent, or Firm*—Wenderoth, Lind & Ponack, L.L.P.

(57) ABSTRACT

The present invention relates to the use of an air-liquid interface culture model using asthmatic bronchial epithelial cells, which exhibit impaired epithelial barrier function. It is proposed to use asthmatic epithelial cultures, in the absence of added Th2 or proinflammatory cytokines such as IL-13, as an in vitro model to screen for agents that can act to improve impaired asthmatic epithelial barrier function. Such agents may have therapeutic utility in asthma patients.

7 Claims, 1 Drawing Sheet

OTHER PUBLICATIONS

S. Montefort et al., "The site of disruption of the bronchial epithelium in asthmatic and non-asthmatic subjects", Thorax, vol. 47, pp. 499-503, 1992.

S. M. Puddicombe et al., "Involvement of the epidermal growth factor receptor in epithelial repair in asthma", FASEB J. vol. 14, pp. 1362-1374, 2000.

S. M. Puddicombe et al., "Increased Expression of $p21^{waf}$ Cyclin-Dependent Kinase Inhibitor in Asthmatic Bronchial Epithelium", Am. J. Respir. Cell Mol. Biol., vol. 28, pp. 61-68, 2003.

S. M. Puddicombe et al., "Characterisation of the Mucosecretory Phenotype Induced in Primary Bronchial Epithelial Cells by Chronic Exposure to IL-13 In Vitro", Am. J. Respir. Crit. Care Med., vol. 167, p. A454, 2003.

S. M. Puddicombe et al., "Asthma-Specific Upregulation of the Gel-Forming Mucin, MUC5AC during Epithelial Differentiation in the Presence of Interleukin (IL-)13", Am. J. Respir. Crit. Care Med., vol. 169, p. A536, 2004.

S. M. Puddicombe et al., Pertinent portions of poster presented by Puddicombe et al. at the America Thoracic Society Meeting, Orlando, USA on May 25, 2004.

H. Yoshisue et al., "Characterization of Ciliated Bronchial Epithelium 1, a Ciliated Cell-Associated Gene Induced During Mucociliary Differentiation", Am. J. Respir. Cell Mol. Biol., vol. 31, pp. 491-500, 2004.

\* cited by examiner

SCREENING ASSAY FOR IMPROVEMENT OF EPITHELIAL BARRIER FUNCTION

FIELD OF THE INVENTION

The present invention relates to the novel use of asthmatic bronchial epithelial cells grown at an air-liquid interface for screening for agents which can improve epithelial barrier function. This in vitro model may lead to identification of therapeutic interventions to improve/protect asthmatic bronchial epithelial barrier function.

BACKGROUND OF THE INVENTION

Asthma is a chronic inflammatory airway disease whose prevalence is increasing worldwide and now affects 20% of children and 11% of adults in the UK. It involves a number of genetic susceptibility genes and is characterised by excessive constriction of the airways, which can be triggered by exposure to common aeroallergens, viral infections, air pollutants and even to innocuous stimuli, resulting in chest tightness, breathlessness, wheeze and cough. The disease is progressive with prolonged inflammatory damage to the airway epithelium and remodelling (structural) changes to the airway walls.

Within the airways, the epithelial cells form a physical barrier to the external environment and produce secretions that protect the airways against environmental insults. A major role of the epithelium is production of mucus secretions which protect the airways by forming a barrier which traps inhaled particulates for clearance via the mucociliary escalator. Airway secretions comprise mucins and a plethora of cytoprotective molecules including antioxidants, antiproteases and defensins that contribute to innate host defence and epithelial barrier function.

The bronchial epithelium is a pseudostratified structure comprising a layer of columnar cells with underlying basal cells that act as a physical barrier to separate the external environment and the internal milieu of the lung. Evidence of a disrupted epithelium in asthma has been observed in status asthmaticus (James et al (1998) Inflammatory mechanisms in asthma, pp 1-26. Eds: Marcel Dekker, New York) and in asthmatic sputum, which contains columnar epithelium as shed 'creola bodies'. Furthermore, biopsies obtained from asthmatic subjects show epithelial damage (Laitinen et al. (1985). Am. Rev. Respir. Dis. 131:599-606; Montefort et al. (1992) Thorax 47:499-503) and enhanced expression of the Epidermal Growth Factor Receptor (EGFR), particularly in areas of damaged epithelium where columnar epithelial cells have been shed leaving only a basal cell layer (Puddicombe et al (2000) FASEB J. 14:1362-74).

Epithelial damage in asthma is thought to occur as a consequence of a number of extrinsic factors such as environmental stimuli and inflammatory cell products which disrupt the epithelial barrier. For example, exposure to pollutants, such as ozone or nitrogen dioxide, result in increased epithelial permeability following exposure (Bayram et al. (2002) Clin. Exp. Allergy 32:1285-92), whilst dust mite allergens, exhibiting protease activity, cause epithelial damage facilitating allergen penetration through the epithelial barrier into the underlying airway tissue leading to initiation of allergic inflammation in atopic individuals. Allergen challenges induce influxes of inflammatory cells, e.g. eosinophils and release of eosinophil basic proteins that further augment epithelial damage (Erpenbeck et al. (2003) Clin. Exp. Allergy 33:331-6). Once damaged, the epithelium in asthma shows little evidence of cell proliferation to restore barrier integrity (Demoly et al. (1994) Am. J. Respir. Crit. Care Med. 150:214-7) and expression of markers associated with growth arrest are observed (Puddicombe et al. (2003) Am. J. Respir. Cell Mol. Biol. 28:61-8). Thus a protracted epithelial repair process in asthma may contribute to the establishment of chronic inflammatory and remodelling responses and to the decline in lung function and respiratory symptoms associated with asthma. Mucus, which acts to provide epithelial protection, is produced in large quantities in asthma. However, in the face of extensive epithelial damage and loss of columnar ciliated epithelial cells, clearance of this mucus is severely reduced and results in formation of mucus plugs within the airways that can impair lung function. Thus, maintenance of the integrity of the epithelium is an important component of airways defence required to prevent epithelial damage in the face of numerous environmental insults.

It has previously been found that by culturing primary bronchial epithelial cells (BECs) obtained from the airways of asthmatics or normal BECs at an air-liquid interface, the cells can be caused to differentiate to provide a fully differentiated epithelium resembling airway epithelium in vivo (Yoshisue et al. (2004) Am. J. Respir. Cell Mol. Biol. 31:491-500). Many studies using an in vitro model system of this type have shown that interleukin-13 (IL-13) and other Th2 cytokines associated with the asthma phenotype can physically alter normal epithelial differentiation to affect the epithelial barrier and its function (Atherton et al (2003) Am. J. Physiol. Lung Cell Mol. Physiol 285:L730-L739). Exposure of epithelial cells to IL-13 during differentiation, either at an air-liquid interface or in spheroid cultures, can result in reduced transepithelial resistance, alterations in tight junctional proteins and impaired epithelial polarity (Laoukili et al. (2001) J. Clin. Invest. 108:1817-24; Kondo et al. (2002) Am. J. Respir. Cell Mol. Biol. 27:536-41). These functional alterations in the epithelial barrier induced as a consequence of Th2 cytokines have suggested the potential utility for anti-cytokine therapies for the improvement of abnormal epithelial function in the face of inflammatory and environmental insults in asthma.

Using an established air-liquid interface culture model system (Puddicombe et al. (2003) Am. J. Respir. Crit. Care Med. 167: A454), the inventors have now made the further unexpected finding that, even in the absence of addition of any Th2 cytokine or damaging agent, asthmatic epithelial cultures exhibit a significantly decreased epithelial barrier integrity as determined by measurement of transepithelial electrical resistance when compared to similar cultures of epithelial cells from non-asthmatic subjects (first reported in a poster presented at The American Thoracic Society meeting, Orlando, USA on 25th May 2004; related abstract: Puddicombe et al. (2004) Am. J. Respir. Crit. Care Med. 169:A536). Whilst barrier function measurements in cultures of bronchial epithelial cells from normal or asthmatic subjects did not significantly differ over the time course examined (see FIG. 1), at all measurement time points at 7 to 21 days from the start of culture, asthmatic bronchial epithelial cell cultures demonstrated a reduced barrier function when compared to bronchial epithelial cells from normal subjects cultured under identical conditions. Thus whilst it was previously known that environmental stimuli and inflammatory cell products will promote bronchial epithelial damage in asthmatics, it is now postulated that the extent of damage observed in asthmatic epithelium may actually be a consequence of, or contributed to by, an additional intrinsic susceptibility independent of any action of Th2 cytokines or detrimental effects of environmental or inflammatory agents.

An increased epithelial permeability in asthma will likely impair epithelial barrier integrity (Puddicombe et al. (2004) Am. J. Respir. Crit. Care Med. 169:A536) and lead to greater penetration of noxious agents into the airway wall with a higher propensity for extensive epithelial damage. Enhanced epithelial permeability to damaging environmental stimuli may also contribute to the known upregulation of mucus containing secretions observed in asthma. Hence, there is now interest in determining agents which will improve or supplement defective barrier function of bronchial epithelium in asthmatics that occurs in the absence of any exogenous Th2 cytokine or other agent to reduce or prevent epithelial permeability leading to promotion of epithelial damage. Asthmatic bronchial epithelial cells differentiated in vitro in the absence of any added Th2 or proinflammatory cytokine coupled with measurement of epithelial barrier function is proposed herein as a novel model system which can be used as a preliminary in vitro screen for such agents.

SUMMARY OF THE INVENTION

More particularly, the present invention provides a method of screening a test agent for ability to improve barrier function of epithelium formed from cultured asthmatic bronchial epithelial cells, which comprises:

(i) providing cultured asthmatic bronchial epithelial cells;

(ii) further culturing said cells on a porous support at an air-liquid interface whereby they differentiate in culture and will form an in vitro epithelium, said culturing being in the absence of any added Th2 or proinflammatory cytokine such as IL-13 and for a period such that an epithelial barrier is detectable;

(iii) adding to the same culture, or an identical culture, either at the start of culturing or during culturing said test agent whereby the test agent is contacted with the epithelial cells;

(iv) and determining at one or more time points after formation of an epithelial barrier is detectable whether said test agent improves epithelial barrier function compared with epithelial barrier function detectable in an identical culture apart from the absence of the test agent.

Detectable epithelial barrier formation may be equated, for example, with measurement of transepithelial electrical resistance significantly above base-level. Typically, first determination of epithelial barrier function will be after visual observation of a continuous monolayer of cells. Generally such observation can be expected by 1 to 5 days from the start of air-liquid interface (ALI) culture.

Generally, determination of epithelial barrier function will be, or include, after attainment of full differentiation and maximum barrier function. Full differentiation equates with observation of a continuous epithelial layer with beating ciliated cells and mucus production. Full differentiation can be expected by days 18-21 with a plateau in measured barrier function expected by days 7-14 using the exemplified air-liquid interface culture system in the absence of any test agent. However, it may prove useful to observe barrier function at earlier time points and to extend the observations of barrier function up to 28 days or more.

Comparison may also desirably be further made with epithelial barrier function detectable in an identical culture of non-asthmatic bronchial epithelial cells. Of particular interest are test agents which will increase or supplement epithelial barrier function of asthmatic bronchial epithelial cells in an in vitro test system as described above so that it attains substantially the same level as observed with non-asthmatic control cells cultured under the same conditions minus the test agent.

BRIEF DESCRIPTION OF THE FIGURE

FIG. 1: Measurement of epithelial barrier function using transepithelial electrical resistance $\Omega \cdot cm^2$) in cultures of asthmatic and non-asthmatic bronchial epithelial cells during their differentiation at an air-liquid interface. Transepithelial electrical resistance (TER) measurements of bronchial epithelial cell cultures were assessed during epithelial cell differentiation and in fully differentiated cultures grown at an air-liquid interface. TER readings were taken at days 7, 14 and 21 after placing cultures at an air-liquid interface using chopstick electrodes with a voltohmmeter and resistance measurements were adjusted to $\Omega \cdot cm^2$. Symbols represent the mean resistance measurements of at least three replicate cultures obtained from each normal or asthmatic subject (n=15/group; for each day, the right hand results are for asthmatic cells); box plots depict the median and 25-75% inter quartile ranges and the error bars depict the 95% confidence limits. Data was analysed using the non-parametric Mann Whitney U test, with $p<0.05$ being considered significant.

DETAILED DESCRIPTION

Figure 1:
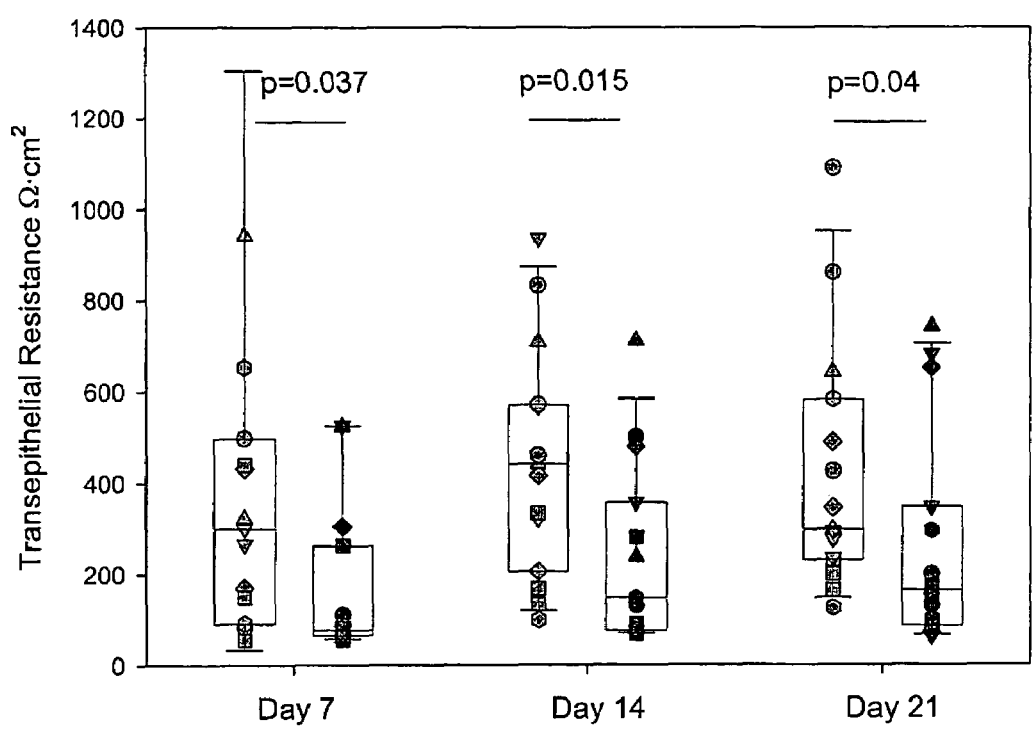
FIG. 1, as already referred to above as foundation for the invention, is now further described below. More detailed description of how the relevant results were obtained is set out in the exemplification for the invention below

Provision of Asthmatic Bronchial Epithelial Cells for Culturing to Form in vitro Epithelium Asthmatic Subjects Asthmatic subjects can be recruited and characterized according to symptoms, lung function, medication and skin prick tests to common aero-allergens. Asthma severity in chosen subjects may be assessed using the Global Initiative for Asthma (GINA) guidelines on the diagnosis and management of asthma (Bousquet J. (2000). Clin. Exp. Allergy 30(1):2-5)

Obtaining of Bronchial Epithelial Cells

Bronchial epithelial cells may, for example, be obtained from asthmatic volunteers using the well-known technique of fibre-optic bronchoscopy to obtain bronchial epithelial cell brushings as further described in the exemplification. Using a sheathed nylon cytology brush, several consecutive brushings may be obtained from the airway mucosa (generally 4-8 brushings) from the 2nd to 3rd generation of bronchi. After each brushing, cells are generally harvested into 5 mls sterile phosphate-buffered saline (PBS) before addition of an equal volume of 20% FBS/RPMI. Brushed cells are then combined, centrifuged at 150×g for 5 mins and the pellet resuspended into Bronchial Epithelium Growth Medium (BEGM; Clonetics, UK) or related media selective for the growth of epithelial cells.

Suitable starting cells may also be obtained in known manner by promotion of epithelial cell out-growths from bronchial biopsies, or enzymatic dispersion of such biopsies, from asthmatic subjects obtained by bronchoscopy. Bronchial epithelial cells may also be obtained by enzymatic dispersion using freshly resected lung tissue (clinical waste) resulting from lung tumour resections from asthmatics or, possibly, after the death of an asthmatic subject. Enzymatically disaggregated lung epithelial cells may again be grown using BEGM or known related media selective for the growth of airway epithelial cells.

Epithelial cell purity and phenotype can be assessed on cell preparations using Rapi-Diff II staining (Diachem Int. Ltd, UK) and immunochemistry for cytokeratins 13 and 18, and MUC5AC.

Primary Bronchial Epithelial Cell Cultures

Cultured bronchial epithelial cells for culture at an air-liquid interface may be obtained by conventional culturing techniques. For the purpose of screening according to the invention, it will generally be found preferable to expand the cells in a primary culture step, more particularly desirably primary monolayer culture, to obtain sufficient cells, then transfer cells to the porous support chosen for ALI culturing as submerged cultures to reach 90 to 100% confluence prior to the start of ALI culture with fresh ALI medium.

Thus, primary cultures may be grown in a humidified incubator at 37° C., 5% $CO_2$ using flasks pre-coated with collagen I and BEGM culture media. In this case, it will be suitable to replenish the growth medium daily for the first three days and thereafter every 2 days. Medium containing unattached cells may be transferred into fresh collagen I coated flasks at 24 h and 48 h to ensure maximal recovery of cells. Epithelial cells can generally be expanded in culture over 2-3 weeks and routinely used for experimentation at passage 2 (p2). At higher passages (greater then p3), the cells may become senescent, but those frozen at early passages such as p1 can be cultured successfully after freezing.

Prior to culturing to promote differentiation, primary cultured cells obtained as above will be trypsinised and may be preferably seeded directly on to the porous support selected for ALI culturing, e.g. a collagen I coated transwell culture insert (Transwell-COL, 6.5 mm, 0.4: µM pore size; Corning Costar, UK). Other proprietary brands of porous membrane inserts may be used which may be either pre-coated or may be coated with collagen I. As indicated above, preferably ALI culturing will be preceded by submerged growth, e.g. in BEGM, until the cells reach 90-100% confluent (generally 1-2 days, although cells may be grown submerged for up to a week or more). The porous support will then be taken to the air-liquid interface for air-liquid interface culturing to promote cell differentiation and epithelium formation.

Bronchial Epithelial Cell Culture at an Air-Liquid Interface (ALI)

Cell culture at an air-liquid interface may be carried out in known manner. Apical medium is removed (day 0 ALI) and basal medium replaced with fresh medium for ALI culturing, which is changed regularly, preferably daily or at least every other day. The following medium was found suitable for ALI culturing by the inventors: 1:1 DMEM (Invitrogen, UK), Bronchial Epithelial Basal Medium (BEBM; Clonetics, UK) supplemented with a final concentration of 0.4% (v/v) bovine pituitary extract, 5 µg/ml insulin, 5 ng/ml hydrocortisone, 10 µg/ml transferrin, 6.5 ng/ml T3, 0.5 µg/ml epinephrine, 0.5 ng/ml epidermal growth factor with the exception of 50 nM retinoic acid and 1.5 µg/ml BSA in a modification of the method of Gray et al. (Gray et al (1996) Am. J. Respir. Cell Mol. Biol. 14:104-12)

Culturing will generally be continued to achieve full differentiation with maximal barrier function although as indicated above determination of the effect of a test agent on barrier function may be made at earlier time points after barrier function becomes detectable.

Measurement of Epithelial Barrier Function

Measurement of transepithelial electrical resistance (TER) is a preferred approach to monitor barrier function of cultured epithelial cells grown on porous supports as above. Transepithelial electrical resistance can be determined, for example, using a voltohmmeter and chopstick electrodes (World Precision Instruments, Sarasota, USA) as further described in the exemplification and is recognised as a straightforward approach to monitor expression and modulation of barrier-forming cell-cell contacts (tight junctions) in cultured cells grown on porous supports. Measured values must be adjusted to take into account baseline resistance and the surface area of the epithelium measured. However, other techniques are known for determining epithelial barrier function and might be employed for the purpose of screening according to the invention. For example, flux of fluorescent or radiolabelled tracer molecules through a formed epithelial layer (i.e. passage between the upper and lower chambers of the culture system for ALI culture) might be monitored. Suitable tracers known for determination of epithelial permeability in this manner include fluorescein isothiocynate-dextran (FITC-dextran) and radiolabelled tracers (such as mannitol, sucrose, inulin) (Mathias et al. (1996) J. Drug Target 4:79-86); West et al. (2002) Cell Commun. Adhes. 9:29-44; Johnson (2005) Ad. Drug Delivery Reviews 57:111-121) It is known that a decline in TER will be reflected in an increased apical to basolateral flux of FITC-dextran or radiolabelled tracer molecules across the epithelial layer. Alternatively, epithelial barrier function may be assessed using Ussing chambers where impedance analysis reveals the ionic permeability of the epithelium (i.e. epithelial resistance) using short-circuited conditions as previously described (Li et al. (2004) J. Cyst. Fibros. 2:123-6). Conductance scanning may also be performed to differentiate transcellular and tight junctional conductance (Gitter et al. (1997) Pflügers Arch. 434:830-840) whilst patch clamping techniques can determine transcellular transport (Hamill (1981) Pflugers Arch. 391:85-100).

As indicated above, determination of epithelial barrier function may be made at one or more time points after formation of an epithelial barrier is detectable. For example, this may be equated with measurement of transepithelial electrical resistance significantly above base-level. Base-level will be dependent on the precise ALI culture system, but generally a TER above 50-100 $\Omega \cdot cm^2$ might be anticipated to be indicative of some barrier function. Typically, first determination of epithelial barrier function will be after visual observation of a continuous monolayer of cells. If the cells provided for ALI culture are highly confluent, a few holes may form on change of medium to the ALI medium but in general a continuous monolayer might be anticipated within 1 to 5 days. Generally, it will be favoured that determination of epithelial barrier function will be, or include, after attainment of fill differentiation and maximum barrier function. With these considerations in mind, it may be favoured to determine epithelial barrier function at one or more time points beyond 5 days, e.g. 7 to 14 days or longer, although it may prove useful to determine barrier function at earlier time points.

Test Agents

Test agents may be agents to be tested for ability to increase inherent barrier function of in vitro asthmatic bronchial epithelium or coating agents which may be of interest for supplementing such barrier function. Test agents may include but are not limited to antibodies, small molecule inhibitors, drugs, natural or synthetic mucosal protective agents, cytokines, growth factors, antioxidants, antiproteases, natural or synthetic airway secretions and mimetics of surfactant or other intervention. The test agent may be added to the ALI culture at any time during culture. The agent may be added either to the apical surface of the culture (upper transwell chamber), to the basolateral surface (lower chamber) or to both.

As indicated above, of particular interest are test agents which will increase or supplement epithelial barrier function of asthmatic bronchial epithelial cells in an in vitro test system of the invention so that it attains substantially the same level as observed with non-asthmatic cells cultured under the same conditions minus the test agent.

The following exemplification further illustrates the invention.

EXAMPLES

Methods

Clinical Characterisation of Subjects

Subjects were characterised according to symptoms, lung function, medication and skin prick test to common aeroallergens. Asthma severity was assessed using the Global Initiative for Asthma (GINA) guidelines on the diagnosis and management of asthma (Bousquet J. (2000) Clin. Exp. Allergy 30 (1):2-5) and BHR determined using methacholine inhalation challenge, and expressed as $PC_{20}$ (the cumulative dose of methacholine required to produce a 20% fall in Forced Expiratory Volume in 1s [$FEV_1$] from baseline values). All volunteers were non-smokers and free from respiratory tract infections for a minimum of 4 weeks prior to inclusion to the study. Written informed consent was obtained from all volunteers prior to participation, and ethical approval for the study was obtained from the Joint Ethics Committee of Southampton University Hospital Trust. Twenty-one non-atopic, normal control volunteers (16 female; age median (range), 25 (19-37); $PC_{20}$>8; % predicted $FEV_1$ (range), 107 (81-120) and twenty-one asthmatic volunteers (9 female; age median (range), 27 (19-37); $PC_{20}$ (range) 3.78 (0.03-16.5); % predicted $FEV_1$ (range), 89.6 (63-104.5)) were recruited. The mean (range) dose of inhaled corticosteroids was 725 µg (200-1600) in asthmatics, with only four of the twenty-one volunteers taking short acting β-agonists alone.

Fibreoptic Bronchoscopy

Bronchial brushings were obtained by fibreoptic bronchoscopy in accordance with standard guidelines (Hurd (1991) J. Allergy Clin. Immunol. 88:808-14) as previously described (Bucchieri et al. (2002) Am. J. Respir. Cell. Mol. Biol 27:179-85). Briefly, under direct vision, a sheathed nylon cytology brush was used to collect 5-8 consecutive brushings from the bronchial mucosa of the second to third generation bronchi. After each brushing, cells were harvested into 5 ml sterile phosphate-buffered saline (PBS) before addition of an equal volume of 20% FBS/RPMI. Brushed cells were combined, centrifuged at 150×g for 5 mins and the pellet resuspended into Bronchial Epithelium Growth Medium (BEGM; Clonetics, UK). Epithelial cell purity and phenotype was routinely assessed on cell cytopreparations using Rapi-Diff II staining (Diachem Int. Ltd, UK) and immunocytochemistry for cytokeratins 13 and 18, and MUC5AC.

Primary Bronchial Epithelial Cell Cultures

Bronchial epithelial cells (BECs) were cultured in a humidified incubator at 37° C., 5% $CO_2$ using flasks pre-coated with collagen (Vitrogen-100; Nutacon, The Netherlands; 30 µg/ml in $dH_2O$) for 1 h, and discarded prior to addition of the cells and BEGM. The growth medium was replenished daily for the first three days and thereafter every 2 days. Media containing unattached BECs was transferred into fresh collagen-coated flasks at 24 h and 48 h to ensure maximal recovery of cells. Blood cell contamination of bronchial brushings was not found to affect subsequent BEC culture. BECs were expanded in culture over 2-3 weeks and routinely used for experimentation at passage 2 (p2) generating approx $1\times10^7$ cells. At higher passages (>p3), the cells became senescent, but those frozen at p1 and subsequently thawed could be cultured successfully.

Air-Liquid Interface Cultures

BECs (p2) were trypsinised and seeded into collagen-coated transwell culture inserts (Transwell-COL, 6.5 mm, 0.4 µM pore size; Corning Costar, UK) in BEGM ($1\times10^5$ cells/insert)(i.e. $3.3\times10^4/cm^2$). The cells were grown submerged until 90-100% confluent, generally 1-2 days, before being taken to the air-liquid interface (ALI).

Apical medium was removed (day 0) and basal medium replaced with 300 µl of ALI medium (1:1 DMEM (Invitrogen, UK): BEBM (Clonetics, UK) supplemented with a final concentration of 0.4% (v/v) bovine pituitary extract, 5 µg/ml insulin, 5 ng/ml hydrocortisone, 10 µg/ml transferrin, 6.5 ng/ml T3, 0.5 µg/ml epinephrine, 0.5 ng/ml epidermal growth factor with the exception of 50 nM retinoic acid and 1.5 µg/ml BSA in a modification of the method of Gray et al. (Gray et al. (1996) Am. J. Respir. Cell. Mol. Biol. 14:104-12). ALI medium was changed daily, except at weekends. Cells were cultured for a period of 21 days after which time a fully differentiated epithelium with beating ciliated cells was observed.

Measurement of Epithelial Barrier Function

Transepithelial electrical resistance (TER) was determined using a voltohmmeter and chopstick electrodes (World Precision Instruments, Sarasota, USA) at days 7, 14 and 21 after culture at an air-liquid interface. Hanks buffered salts solution (HBSS;100 µl) warmed to room temperature was placed into the upper chamber of the transwell and the cells were allowed to adjust to the effects of the medium change for a period of 20 mins. After this time, the long arm of the chopstick electrode was placed in contact with the medium in the lower chamber and the short arm placed into the medium in the upper transwell chamber. In this way transepithelial electrical resistance measurements were taken across the epithelium cultured in the transwells and resistance measurements were recorded. Values were then adjusted to account for baseline resistance and the surface area of the epithelium being measured. The Hanks buffered saline solution can then be used to wash the surface of the cells and is carefully removed from the upper chamber using a fine tipped pastette, so as not to physically damage or disrupt the epithelial layer. Once the HBSS is removed, the cells are again cultured at an ALI and cultures are capable of withstanding a washing step without affecting the structure of the epithelium or subsequent TER readings.

Results

Epithelial barrier integrity was assessed in normal and asthmatic cultures using transepithelial electrical resistance measured at days 7, day 14 and day 21. Within normal or asthmatic cultures, there was no significant difference in the transepithelial electrical resistance measurements when assessed at each of the time points using the non parametric Kruskal Wallis test (data not shown). However, asthmatic cultures did show significantly decreased TER readings when compared to normals at each of the time points (see FIG. 1), data analysed using the non parametric Mann Whitney U test. At day 21, transepithelial electrical resistances determined in fully differentiated cultures of BECs from asthmatic patients were 164.43 (60.92-739.71) compared to 297.74 (98.91-934.45) for the control cultures, p=0.04 median (range) respectively (n=15 subjects/group); see FIG. 1. This disease-specific reduction in transepithelial electrical resistance suggests an intrinsic defect in epithelial barrier integrity and function in asthma. This increase in epithelial permeability in asthma may therefore contribute to an increased susceptibility to the damaging effects of environmental agents.

We claim:

1. A method of screening a test agent for ability to improve barrier function of epithelium formed from cultured asthmatic bronchial epithelial cells, which comprises:
   (i) providing cultured asthmatic bronchial epithelial cells;
   (ii) further culturing said cells on a porous support at an air-liquid interface whereby they differentiate in culture and will form an in vitro epithelium, said culturing being in the absence of any added Th2 or proinflammatory cytokine and for a period such that an epithelial barrier is detectable;
   (iii) adding to the culture, either at the start of culturing or during culturing said test agent whereby the test agent is contacted with the epithelial cells;
   (iv) and determining at one or more time points after formation of an epithelial barrier is detectable whether said test agent improves epithelial barrier function compared with epithelial barrier function detectable in an identical culture without the test agent.

2. A method as claimed in claim 1 wherein said determining is performed by transepithelial electrical resistance measurement.

3. A method as claimed in claim 1 wherein said determining is performed after visually observing a continuous monolayer of cells.

4. A method as claimed in claim 1 wherein said determining is, performed after attaining full differentiation and maximum epithelial barrier function.

5. A method as claimed in claim 1 wherein said determining includes determining epithelial barrier function at one or more time points at 7 days or longer from the start of air-liquid interface culturing.

6. A method as claimed in claim 1 wherein the providing of cultured asthmatic bronchial epithelial cells for air-liquid interface culturing in step (i) comprises (a) growing isolated asthmatic bronchial epithelial cells in a primary culturing step, (b) transferring cells to said porous support and (c) performing submerged culturing of the cells on said support to reach 90 to 100% confluence prior to step (ii).

7. A method as claimed in claim 1 wherein said test agent is a coating agent.

* * * * *